(12) United States Patent
Mercelis et al.

(10) Patent No.: US 9,681,867 B2
(45) Date of Patent: Jun. 20, 2017

(54) COSMETIC IMPLANT (71) Applicant: LAYERWISE N.V., Heverlee (BE)

(72) Inventors: Peter Mercelis, Heverlee (BE); Gwen Swennen, Knokke-Heist (BE)

( * ) Notice: Subject to any disclaimer, the term of this patent is extended or adjusted under 35 U.S.C. 154(b) by 286 days.

(21) Appl. No.: 14/379,037

(22) PCT Filed: Feb. 15, 2013

(86) PCT No.: PCT/BE2013/000007
§ 371 (c)(1),
(2) Date: Aug. 15, 2014

(87) PCT Pub. No.: WO2013/120150
PCT Pub. Date: Aug. 22, 2013

(65) Prior Publication Data
US 2015/0032134 A1 Jan. 29, 2015

(30) Foreign Application Priority Data
Feb. 15, 2012 (BE) .................................. 2012/0095

(51) Int. Cl.
*A61B 17/04* (2006.01)
*A61B 17/00* (2006.01)
(Continued)

(52) U.S. Cl.
CPC ...... *A61B 17/0487* (2013.01); *A61B 17/0401* (2013.01); *A61B 17/80* (2013.01);
(Continued)

(58) Field of Classification Search
CPC . A61B 17/0401; A61B 17/0487; A61B 17/80; A61B 17/8004; A61B 17/8009;
(Continued)

(56) References Cited

U.S. PATENT DOCUMENTS

| | | | |
|---|---|---|---|
| 6,471,715 B1 * | 10/2002 | Weiss | A61B 17/04 606/216 |
| 2007/0156175 A1 * | 7/2007 | Weadock | A61B 17/0401 606/216 |

(Continued)

*Primary Examiner* — Ryan J Severson
*Assistant Examiner* — Christian Knauss
(74) *Attorney, Agent, or Firm* — Browdy and Neimark, PLLC (57) ABSTRACT

The invention concerns an implant for adjusting the position of at least one tissue holder (6) for soft tissue, whereby this implant can be fixed to bone tissue at a distance from said tissue holder (6) and has a guide (3) for an elongate pulling member (4), whereby this pulling member (4) is connected to said tissue holder (6), and whereby the implant includes a fixing element (10) which can be moved between a fixing position in which the pulling member (4) is clamped by the fixing element (10) and a free position in which said pulling member (4) can freely move through said guide (3), characterized in that said fixing element (10) cooperates with a control element (14) which makes it possible to move this fixing element (10) between said fixing position and said free position when the implant is attached to said bone tissue and when the implant is covered with soft tissue such as muscle tissue or skin tissue.

23 Claims, 4 Drawing Sheets

(51) Int. Cl.
   *A61B 17/06* (2006.01)
   *A61B 17/80* (2006.01)
(52) U.S. Cl.
   CPC ............... *A61B 2017/00792* (2013.01); *A61B 2017/00867* (2013.01); *A61B 2017/0451* (2013.01); *A61B 2017/0496* (2013.01); *A61B 2017/06176* (2013.01)
(58) Field of Classification Search
   CPC .. A61B 2017/00792; A61B 2017/0451; A61B 2017/0496; A61B 2017/00867; A61B 2017/06176; A44B 19/303
   USPC .................................................. 606/215–218
   See application file for complete search history.

(56) References Cited

U.S. PATENT DOCUMENTS

2007/0173887 A1\* 7/2007 Sasaki ................ A61B 17/0401
                                                   606/232
2008/0132944 A1\* 6/2008 Kress ................ A61B 17/0487
                                                   606/228

\* cited by examiner

COSMETIC IMPLANT

The invention concerns an implant which can be used in the execution of cosmetic surgeries, such as for example facelifts. Soft tissue such as skin tissue or muscle tissue is hereby displaced somewhat in order to make wrinkles and folds of for example the facial skin less noticeable or to remove them. When performing a facelift, for example, the facial skin is detached from deeper tissue layers and then tightened and fixed in one way or another, for example with the aid of a tissue holder acting on the detached facial skin and which is connected to the bone of the skull.

The present invention concerns an implant for connecting at least one tissue holder to the bone tissue and for adjusting the position of at least one tissue holder for soft tissue, whereby said implant can be fixed to bone tissue at a distance from said tissue holder and has a guide for an elongate pulling member, whereby this pulling member is connected to said tissue holder. The implant has a fixing element which is movable between a fixing position wherein the pulling member is clamped by the fixing element and a free position wherein said pulling member is freely movable through said guide.

According to the present state of the art there are different ways to stretch or move skin tissue. This is done for example by manually fixing a suture thread to the tissue and then anchoring this thread to the bone of the skull or other tissues. Use is also made of tissue holders which may take the form of a wire or a plate with one or more barbs which engage into the soft tissue. The wire or the plate is fixed to the bone tissue during surgery, for example with the aid of a screw.

All these systems according to the present state of the art are disadvantageous, however, in that there is a risk for the skin tissue to be moved or stretched too much or too little whereby it is no longer possible to correct the operation after the surgery without a new surgical intervention. Thus, for example, such a surgery is normally performed while the patient is lying down or in other words is in a horizontal position. When the patient stands upright after completion of the operation, it sometimes appears that the desired result does not correspond to the obtained result of the operation. In addition, swellings may arise during the surgery, which may possibly contribute to making a facial correction impossible or extremely difficult.

Document US 2008/0132944 describes an implant which is anchored to the skull's bone to perform what is called a facelift. With the help of this implant, a thread can only be moved in one direction in relation to the implant, and consequently, a correction of the surgery in the opposite direction is impossible.

In other systems which are used in heart valve surgery, such as described for example in documents US 2007/0051377 and US 2004/0133274, use is made of a locking system which allows for a thread to be moved in opposite directions and to fix it in a reversible manner. These systems are relatively complex and voluminous, however, which makes them not suitable for use in cosmetic applications where they must be fixed to the skull's bone under the skin. In addition, these systems require the use of a relatively thick thread provided with thickenings or recesses.

The invention aims to remedy these disadvantages by providing an implant which makes it possible to correct the performed surgery post-operatively. In particular, the invention aims to provide a system and an implant which make it possible to adjust the movement of skin tissue, preferably in a reversible manner, without any surgery being required and even after the skin was closed over the inserted tissue holders or implants.

In addition, the invention aims to provide a highly compact implant whose presence, once fixed to the skull, does not interfere and is not noticeable and allows for a very thin thread, such as for example a surgical suture, to be fixed in relation to the implant.

To this aim, said fixing element cooperates with a control element which makes it possible to move the fixing element between said fixing position and said free position once the implant has been fixed to said bone tissue and once the implant has been covered with soft tissue such as muscle tissue or skin tissue.

Practically, the implant according to the invention contains a clamping element extending opposite said fixing element, whereby said pulling member extends between said clamping element and the fixing element, such that in said fixing position, the pulling member is clamped between the fixing element and the clamping element and, in said free position, the pulling member can be moved according to its longitudinal direction between the fixing element and the clamping element.

Advantageously, said fixing element has two opposing parts, a first part of which is connected to a base of the implant, whereas the second part of the fixing element can be moved in relation to said base, whereby this second part, in said fixing position, clamps the pulling member and whereby, in said free position, the pulling member can be freely moved along this second part.

According to a preferred embodiment of the implant according to the invention, said control element includes a control wire which is connected to the fixing element.

According to an advantageous embodiment of the implant according to the invention, it contains a guide for said control wire through which the latter must extend, whereby this guide ends in said fixing element.

According to an interesting embodiment of the implant according to the invention, at least said fixing element is made of a Shape Memory Alloy or a bimetal, whereby said control element is formed of a cold or heat source which makes it possible to bring the fixing element at a temperature which is different from the body temperature, such that this fixing element is transformed and is moved from said fixing position into said free position.

In a specific embodiment of the implant according to the invention, said first part of the fixing element is hinge-mounted to said base of the implant.

According to a variant of this embodiment of the implant, said first part of the fixing element is rigidly connected to said base, and the fixing element is elastically deformable at least in a zone between the first and the second part thereof, such that the second part can be moved in relation to the first part.

In yet another embodiment of the implant according to the invention, it has a recess in which said fixing element is freely moveable between said fixing position and said free position, and whereby said guide for the pulling member opens in this recess, such that the pulling member extends through this recess.

In an advantageous manner, said guide for the pulling member is interrupted at the height of said fixing element, such that, at least in said fixing position, this fixing element extends at least partly in this interruption.

Other particularities and advantages of the invention will become clear from the following description of a few embodiments of the implant according to the invention; this description is given as an example only and does not limit the scope of the claimed protection in any way; the reference figures used hereafter refer to the accompanying drawings.

In the different figures, the same reference numerals refer to identical or analogous elements.

The invention generally concerns an implant which is used when performing a so-called facial correction or a facelift, whereby soft tissue, such as skin tissue, is stretched and/or moved. To this end, a tissue holder is inserted under the skin which engages in the soft tissue under the skin surface, such that a tensile force can be exerted on this tissue.

According to the invention, said tissue holder is fixed by means of an elongate pulling member to the implant which is fixed to the patient's bone tissue. The pulling member is preferably formed of a wire, but it may also have other shapes and can thus be formed for example of a flat ribbon, a tape-like material, etc.

By tissue holder is meant in this description any element which can be connected to the implant with the aid of a pulling member, such as a wire. Thus, a tissue holder may be formed for example of a flat plate on which are provided sharp, inclined protrusions whose far ends are oriented in the direction of the implant. These protrusions thus form barbs which can engage in the soft tissue under the skin surface. The tissue holder can also be formed of a longitudinal element on which are provided barbs which can engage in the soft tissue. The tissue holder may also be simply formed of a wire having a hook at its far end or which is attached to the soft tissue under the skin.

Said pulling member according to the invention is preferably formed of a wire having a diameter which is smaller than 1.3 mm, for example a diameter which is maximally 1 mm. Normally, a wire is selected for the pulling member whose diameter is smaller than or equal to 0.5 mm.

Thanks to the specific characteristics of the implant, as will be described hereafter, it can be designed in a very compact manner and it will have a volume which is for example smaller than 15×15×2 mm$^3$ or, preferably, a volume which is smaller than 10×10×2 mm$^3$. More specifically, this implant preferably has a base with a length and a width which are each smaller than 15 mm, and preferably smaller than 10 mm, whereby the height of the implant is preferably smaller than 2 mm.

Figure 1:
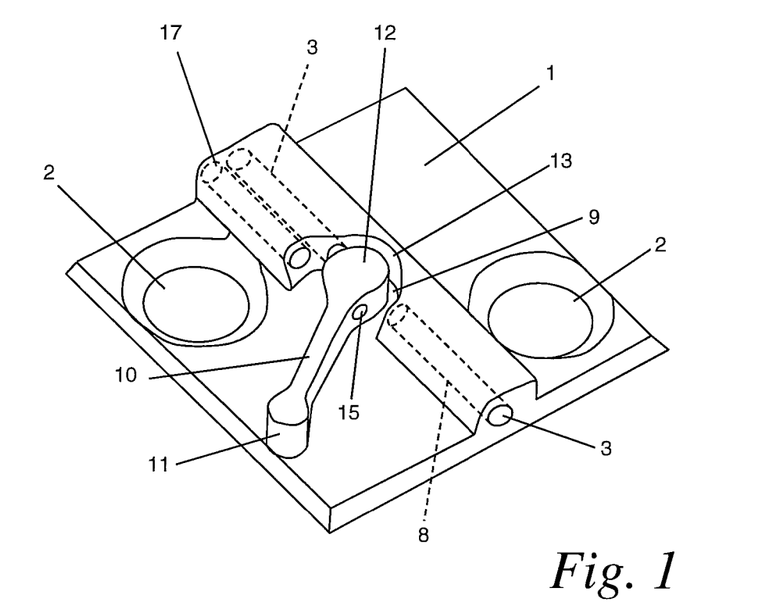
FIG. 1 is a schematic perspective view of an implant according to a first embodiment of the invention.
Figure 2:
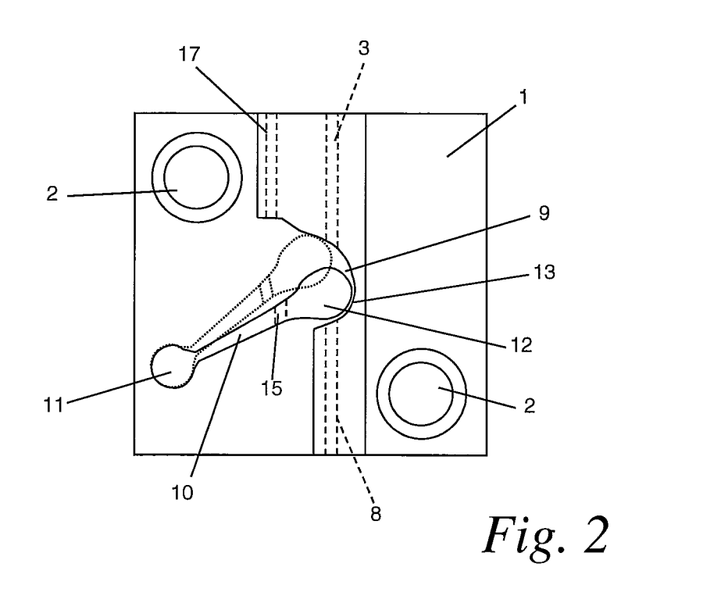
FIG. 2 is a schematic top view of an implant similar to that in FIG. 1.
Figure 3:
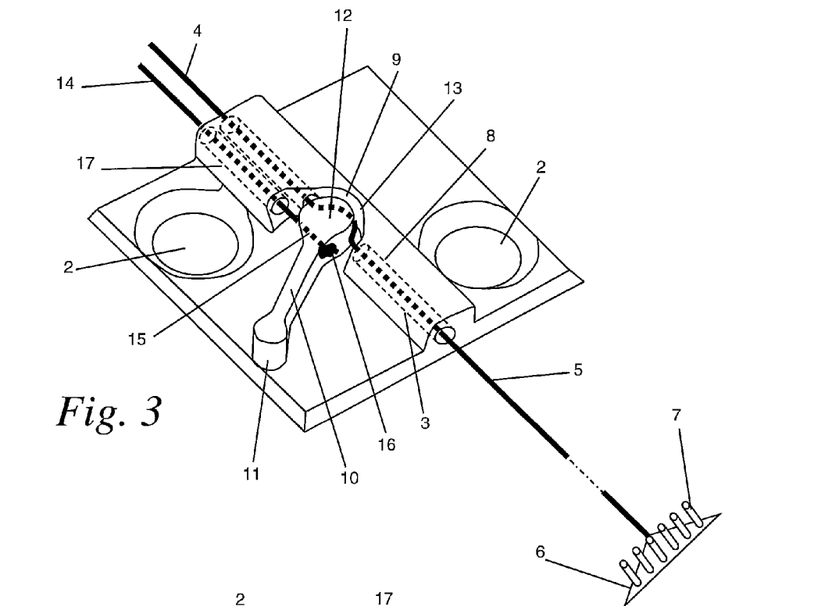
FIG. 3 corresponds to the perspective view of the implant in FIG. 1 which schematically represents a pulling member in the shape of a wire and a control wire.

The implant according to the invention, as represented in FIGS. 1 to 3, makes it possible to adjust the position of one or several tissue holders after completion of the surgery whereby the tissue holders have been inserted under the skin.

This implant has a base 1 which, more specifically, is plate-shaped and has drill holes 2 through which screws can be fixed in a patient's bone tissue so as to fasten the implant to the bone of the skull, for example.

Further, this implant has a guide 3 for an elongate pulling member 4. This pulling member 4 is preferably formed of a wire 5 as represented in FIG. 3. The far end of the pulling member 4 or in other words the wire 5 opposite to the implant is connected to a tissue holder 6.

This tissue holder 6 is formed of a triangular plate which is provided with a row of pins 7 which is somewhat inclined in relation to the plate, such that they form barbs when a tensile force is exerted on the tissue holder 6 by means of the wire 5. Thus, these pins 7 can engage in the soft tissue under the skin. Consequently, by pulling the wire 5, the skin can be moved so as to stretch it for example.

The implant is fixed to the bone tissue at a distance from the tissue holder 6, such that the wire 5 connects the implant to the tissue holder 6.

Said guide 3 for the pulling member 4 forms a tubular channel 8 with a circular cross section. This guide 3 has an interruption 9 where the pulling member 4 runs along a fixing element 10.

This fixing element 10 has an elongated shape and has two opposing parts 11 and 12. A first part 11 is connected to said base 1 of the implant, whereas the second part 12 thereof can be moved in relation to the base 1. More specifically, the first part 11 is hinge-mounted to the base 1. Thus, the fixing element 10 can move over the base 1 around an axis extending vertically in relation to the latter.

In this way, the fixing element 10 can move between a fixing position in which the pulling member 4 is being clamped by the fixing element 10 and a free position in which said pulling member 4 can freely move through said guide 3.

FIG. 2 schematically represents said fixing position of the fixing element 10, shown as a full line, whereas its free position is illustrated by a dotted line. Thus, the second part 12 of the fixing element 10 clamps the pulling member 4 in said fixing position, and the pulling member 4 can freely move along this second part 12 in said free position.

Said interruption 9 of the guide 3 is provided at the height of the fixing element 10, more specifically near said second part 12, such that, at least in said fixing position, this fixing element 10 extends at least partly in this interruption 9.

Further, the implant according to the embodiment of the invention from FIGS. 1 to 3 is provided with a clamping element 13 which extends opposite the fixing element 10. The pulling member 4 extends between this clamping element 13 and the fixing element 10, more specifically said second part 12. This makes sure that, in said fixing position, the pulling member 4 is clamped between the fixing element 10 and the clamping element 13, and that in said free position the pulling member 4 can be moved according to its longitudinal direction between the fixing element 10 and the clamping element 4.

In this particular case, the clamping element 13 is formed of a wall extending almost vertically in relation to said base 1. The corresponding lateral surface of the fixing element 10, more specifically of said second part 12, also extends vertically in relation to the base 1, such that this lateral surface, in said fixing position, connects in a practically fitting manner to the clamping element 13. In this way, the pulling member 4 in the fixing position is clamped sufficiently tight between the clamping element 13 and the fixing element 10 so as to prevent the pulling member 4 from moving as a result of any tensile force being exerted by the tissue holder 6.

In order to adjust the position of the tissue holder 6, the implant is further provided with a control element which makes it possible to move the fixing element 10 between said fixing position and said free position once the implant has been fastened to the bone tissue and once the implant is covered with soft tissue such as muscle tissue or skin tissue.

This control element, in the embodiment of the implant represented in FIG. 3, is formed of a control wire 14 which is connected to the fixing element 10. To this end, the fixing element 10 has a cylindrical bore 15 situated between the first part 11 and the second part 12 thereof and through which said control wire 14 extends and is held by means of a knot 16.

The base 1 of the implant is also provided with a guide 17 for said control wire 14. This guide 17 forms a tubular channel and opens in said fixing element 10.

By exerting a tensile force on the control wire 14 on the far ends thereof opposite the fixing element 10, the latter is moved from the fixing position to the free position, and the pulling member 4 can thus be moved so as to adjust the position of the tissue holder 6.

When no tensile force is exerted on the control wire 14, the fixing element 10 automatically moves into the fixing position under the influence of the pulling member 4. Indeed, the pulling member 4 is connected to the tissue holder 6 which engages in the soft tissue which has been stretched and moved. Consequently, this soft tissue will exert a tensile force on the pulling member 4 via the tissue holder 6. As a consequence, the pulling member 4 which runs over said second part 12 of the fixing element 10 will move the latter into the fixing position when the control wire 14 is not being pulled at.

According to an interesting variant of this embodiment of the implant according to the invention, the fixing element 10, or its connection to the base 1, is made somewhat elastically, such that it moves into said fixing position when no tensile force is being exerted on the fixing element 10 by the control wire 14. The elastic resilience of the fixing element 10 thus makes sure that the pulling member 4 is clamped against said clamping element 13, even when no tensile force is being exerted on the pulling member 4. In such a case, it is for example made sure that the free space between the fixing element 10 and the clamping element 13, in a non-actuated condition, is smaller than the diameter of the pulling wire 4. By this non-actuated condition is understood that no force is being exerted on the fixing element by the control wire 4 and that there is no pulling wire 4 between the fixing element 10 and the clamping element 13.

When the fixing element 10 is controlled by a control wire 14, this implies a wire which preferably has a higher stretch strength than said pulling wire 4. Thus, the control wire 14 may possibly have a larger diameter than the pulling wire 4, or it is made of a material having a higher tensile strength than the material of the pulling wire 4. The control wire 14 has for example a diameter which is smaller than 1.5 mm, and it has for example a diameter which is maximally 1 mm. In some cases, however, it is possible that a wire is selected as a control wire whose diameter is smaller than or equal to 0.5 mm, or that this control wire is identical to the pulling wire.

Figure 5:
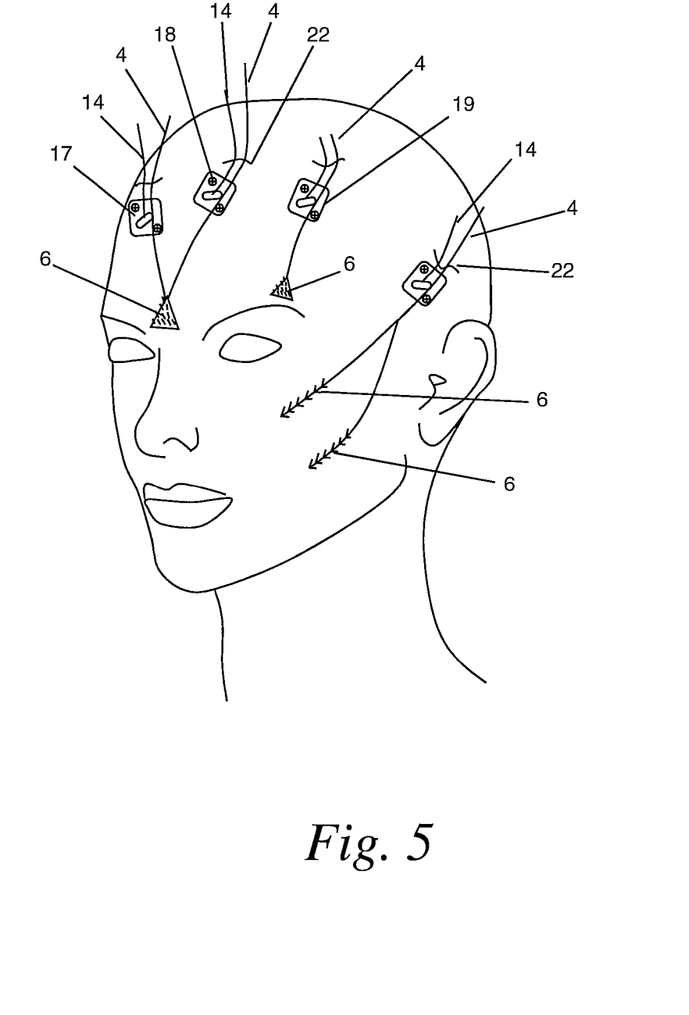
FIG. 5 is a schematic view of the head of a patient which schematically represents different implants according to the invention.

FIG. 5 shows some examples of applications of the implant according to the invention. These implants 17, 18, 19 and 20 were implanted under the skin tissue against the bone of the skull during a surgery, and consequently they are no longer directly accessible without performing a new surgery. However, the corresponding control wires 14 and pulling members 4 extend through a small incision 22 above the surface of the skin, such that they are freely accessible and can be manipulated.

Thus, two implants 17 and 18 are fixed to the bone of the skull by means of screws 21 after a surgery. Each of these implants 17 and 18 is connected to one and the same tissue holder 6 by means of a pull member 4 which engages in the tissue under the skin surface above the nose. Thus, with the aid of the respective control wires 14 of the implants 17 and 18, it is possible to move the tissue holder in the vertical or horizontal direction. The force which is exerted on the tissue holder 6 by each of the pulling members 4 is hereby adjusted.

Further, this figure shows an implant 19 which cooperates with only one tissue holder 6 inserted above an eyebrow under the skin. This implant thus allows for the tissue holder 6 to be moved according to the vertical direction and to thus move the eyebrow up or down accordingly.

Another implant 20 has a pulling member 4 which is connected to two tissue holders 6. These tissue holders 6 are formed of elongated elements on which are provided barbs which engage in the soft tissue under the skin. By moving the fixing device of this implant 20 by means of the control wire 14, the cheek's skin can thus be stretched more or less.

Once the required corrections of the positions of the tissue holders 6 have been implemented, the far ends of the control wires 14 and of the pulling members 4 protruding from the skin can be cut and the incisions 22 are closed. Alternatively, these far ends can be fixed subcutaneously to the bone of the skull or they can be simply put under the skin before the incisions are closed. Thus, if desired, after a period of time, the positions of the tissue holders 6 can possibly be adjusted by simply making a small incision in order to make the far ends concerned accessible again without having to open an entire flap of skin above the implants.

Figure 4:
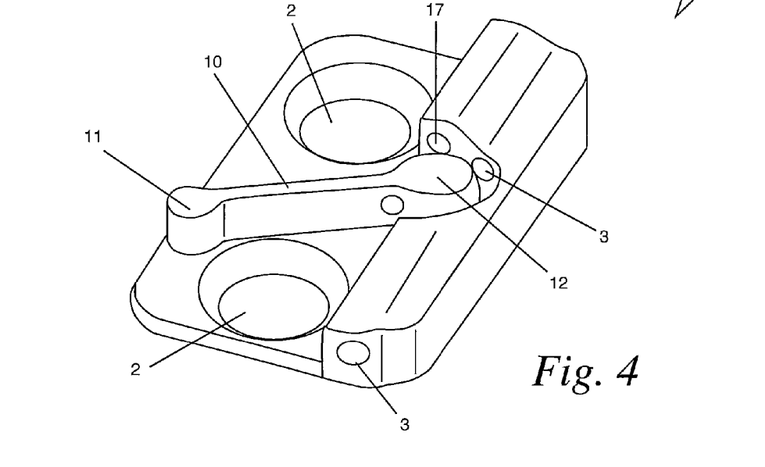
FIG. 4 is a perspective view of an alternative embodiment of the implant according to the invention in FIG. 1.

FIG. 4 shows a variant of the implant according to the invention. This embodiment differs from the preceding one as far as the shape of the base 1 is concerned.

Further, said first part 11 of the fixing element 10 is solidly connected to the base 1, and the fixing element 10 is elastically deformable at least in a zone between the first 11 and the second part 12 thereof. Thus, this second part can relatively move in relation to the first part.

In that case, the fixing element 10 moves between said fixing position and said free position by undergoing an elastic deformation.

According to yet another embodiment of the implant according to the invention, it has a recess in which the fixing element 10 can move freely between said fixing position and said free position. The fixing element need not necessarily be elongate, but it may have the shape of a flat round or prismatic disk, or it may possibly be ring-shaped. The recess in which the fixing element is then situated preferably has means to guide the fixing element during its movement between the fixing position and the free position. This guide also makes sure that the fixing element cannot accidentally come out of the recess. Further, said guide for the pulling member opens in the recess, such that the pulling member extends through this recess up to the fixing element.

Figure 6:
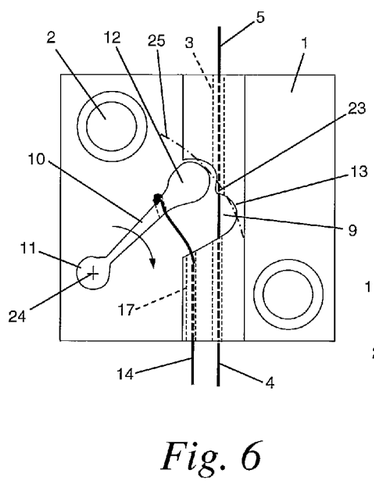
FIG. 6 is a schematic top view of yet another embodiment of the implant according to the invention in which the fixing element is in a free position.
Figure 7:
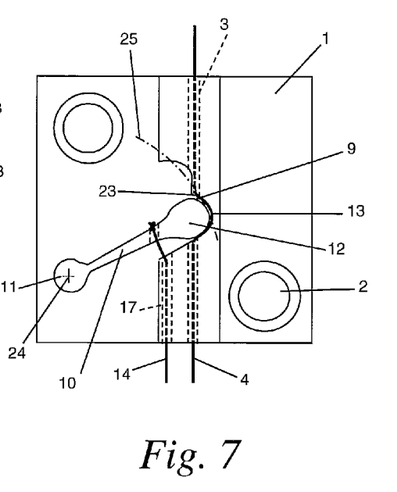
FIG. 7 is a schematic top view of the implant according to the embodiment in FIG. 6, in which the fixing element is in a fixing position.

FIGS. 6 and 7 show an embodiment of the implant according to the invention in which the fixing element 10 can be moved between a fixing position and a free position.

FIG. 6 represents this free position, whereby the pulling member 4 can move freely through the guide 3 thereof. In this free position, the movement of the pulling member 4 according to the longitudinal direction thereof is practically not hindered by the presence of the implant.

Once the pulling member 4 has acquired a definitive position and no longer needs to be moved, the fixing element 10 is brought into said fixing position by exerting a tensile force on the control wire 14 connected thereto. The fixing element 10 with said second part 12 thereof is hereby moved over a projection 23 towards the clamping element 13. When this second part 12 is moved over the projection 23, the fixing element 10 will deform for example in a somewhat elastic manner.

While the fixing element 10 is moved, it rotates around its hinge axis 24, and the far end thereof opposite the hinge axis 24 describes a circular arc 25. The projection 23 hereby extends over a small distance up to the inner side of the circular arc 25.

The clamping element 13 connects to the projection 23 and extends at said interruption 9 of the guide 3 of the pulling member 4. More specifically, this clamping element 13 forms a wall extending almost vertically in relation to the base 1 and onto which said second part 12, possibly with a small clearance, fits closely in said fixing position. Said clearance is preferably smaller than the diameter of the pulling member 4. Consequently, in the fixing position, the pulling member 4 is clamped between the fixing element 10 and the clamping element 13, such that it can no longer move.

The projection 23 thus makes sure that the fixing element 10 cannot be moved back from the fixing position into the free position.

Naturally, the projection 23 can be made in different ways whereby this projection 23 makes sure that the fixing element cannot move from said fixing position into the free position. Thus, the projection 23 may for example be provided on the base 1 of the implant, whereby the fixing device 10 moves over this projection 23 during its movement from said free position into the fixing position, and thus forms a stop which prevents the fixing element from moving back into the free position.

The projection may for example also be secured to the fixing element on the side which is directed towards the base 1. In such a case, a recess is provided for example in the base 1 in which said projection drops when the fixing element is situated in the fixing position, such that the latter is fixed in a permanent position.

In certain cases, however, the implant can be made such that when an external force is exerted on the projection or on the fixing element, for example by said control wire, the fixing element will nevertheless move over the projection into said free position.

Said second part 12 of the fixing element 10 preferably has a bent surface on the side which is directed towards the clamping element 13, whereby the clamping element 13 also has a bent surface, such that said pulling wire 4 is clamped over the entire length of the clamping element 13 between the latter and said second part and is thus fixed. The clamping element 13, the pulling wire 4 and said second part 12 hereby fit tightly against one another.

According to yet another embodiment of the implant according to the invention, the fixing element is made of a memory metal or a bimetal, and said control element is formed of a cold or heat source which allows to bring the fixing element at a temperature which is different from the body temperature, such that this fixing element is transformed and is moved from said fixing position into said free position.

Such a cold or heat source may for example be formed of a cold or hot compress which is put against the skin above the implant in order to obtain the desired temperature change of the fixing element.

Figure 8:
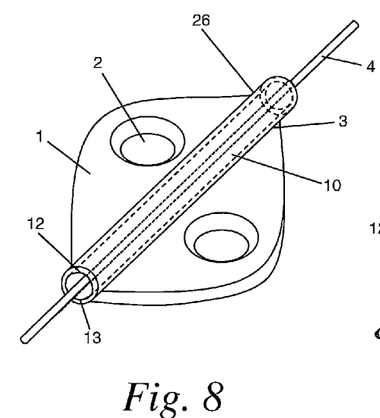
FIG. 8 is a schematic perspective view of an implant according to the invention, with a tubular fixing element in a free position and made of a memory metal.
Figure 9:
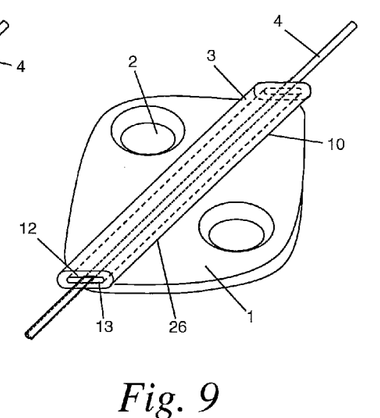
FIG. 9 is a perspective view of the implant in FIG. 8, whereby the fixing element is in a fixing position.

FIGS. 8 and 9 show an example of an embodiment of the implant according to the invention whereby use is made of a memory metal. This implant has a plate-shaped base 1 in which are provided two drill holes 2 in order to be anchored to the bone tissue.

On this base 1 is attached a guide 3 for the pulling wire 4 formed of a tube 26. The tube 26 is made of a memory metal and can be brought from a free position into a fixing position, and vice versa, by bringing a cold or heat source close to the implant. Thus this tube 26, through which said pulling wire 4 extends, forms said fixing element.

FIG. 8 represents this fixing element 10 in a free position whereby the tube 26 has an almost circular section and whereby the pulling member 4 can move almost freely through this tube 26 according to its longitudinal direction. When the fixing element 10 is in said fixing position, the tube 26 is slightly flattened and compressed, whereby the pulling member 4 is clamped between opposite parts of the inner wall of the tube 26, as is shown in FIG. 9. Thus, these opposite parts of the inner wall of the tube 26 form said clamping element 13 and said second part 12 of the fixing element.

Various alternative embodiments may be considered for the implant according to the invention, whereby use is made of a memory metal whereby it is put from a free position into a fixing position so as to clamp the pulling member 4. Naturally, it is not required that the whole implant is made of a memory metal, and for example only a fixing element can be made of a memory metal.

It is also possible to use a synthetic material with memory effect instead of a memory metal.

Advantageously, it is made sure that in said fixing position, the contact surface between the fixing element 10 and the pulling wire 4 on the one hand, and between this pulling wire 4 and the clamping element 13 on the other hand, has no sharp edges or protrusions. To this end, the fixing element 10 and the clamping element 13 are for example made smooth at said contact surface. Thus is avoided that the pulling wire 4 might be damaged, which would shorten its life. As the contact surfaces concerned of the fixing element and clamping element are made smooth, the resistance to displacement of the pulling wire in the fixing position is also improved.

In order to optimize the clamping of the pulling wire 4, such that the wire 4 encounters the greatest possible resistance to displacement, said fixing element 10 and said clamping element 13 preferably have a bent surface at said contact surface, such that in said fixing position, the fixing element 10, the pulling wire 4 and the clamping element 13 connect in a fitting manner. The pulling wire 4 is hereby bent according to a curve, which increases the resistance against displacement of the pulling wire.

Naturally, the invention is not restricted to the above-described embodiments of the implant according to the invention represented in the accompanying drawings. It goes without saying that within the scope of the invention, many variants are possible, more specifically as far as the shape of the fixing element, the clamping element, said projection or the base, etc. is concerned Thus, the implant cannot only be used for performing facial corrections or facelifts, but it can be applied on all parts of the body where soft tissue is to be moved or supported.

It is for example also possible to use a pulling member which forms a wire having a series of constrictions and bulges in its longitudinal direction. Thus, the fixing element can engage in these constrictions in the fixing position.

The implant according to the invention may for example be made of a synthetic material or metal. The implant is preferably produced by applying an additive layer manufacturing technique, such as for example selective laser melting or selective laser sintering of a metal such as for example titanium or a titanium alloy.

Further, the implant can also be manufactured for example by CNC milling or by laser welding the various constituent parts. The implant must not necessarily be produced by applying an additive layer manufacturing technique.

The invention claimed is:

1. An implant for adjusting the position of at least one tissue holder (6) for soft tissue, whereby the implant comprises a base (1) with drill holes (2) through which screws are configured to be fixed in a patient's bone tissue so as to fasten the implant to bone tissue at a distance from said tissue holder (6), wherein the implant has a guide (3) for an elongate pulling member (4), the pulling member (4) being connected to said tissue holder (6), and whereby the implant includes a fixing element (10) which can be moved between a fixing position in which the pulling member (4) is clamped by the fixing element (10) and a free position in which said pulling member (4) can freely move through said guide (3), wherein said fixing element (10) cooperates with a control element (14) which makes it possible to move said fixing element (10) between said fixing position and said free position when the implant is attached to said bone tissue and when the implant is covered with soft tissue, wherein said implant comprises a clamping element (13) formed of a wall extending opposite said fixing element (10) and vertically in relation to said base (1), whereby said pulling member (4) extends between said clamping element (13) and the fixing element (10), such that in said fixing position, the pulling member (4) is clamped between the fixing element (10) and the clamping element (13), and in said free position, the pulling member (4) can be moved according to its longitudinal direction between the fixing element (10) and the clamping element (13).

2. The implant according to claim 1, wherein said fixing element (10) has two opposing parts (11,12), a first part (11) of which is connected to said base (1) of the implant, whereas a second part (12) of the fixing element (10) can be moved in relation to said base (1), wherein said second part (12) clamps the pulling member (4) in said fixing position and wherein, in said free position, the pulling member (4) can be freely moved along said second part (12).

3. The implant according to claim 2, wherein said first part (11) of the fixing element (10) is hinge-mounted to said base (1).

4. The implant according to claim 2, wherein said first part (11) of the fixing element (10) is solidly connected to said base (1) and wherein the fixing element (10) is elastically deformable at least in a zone between the first and the second part thereof, such that the second part (12) can be moved in relation to the first part (11).

5. The implant according to claim 1, further comprising a recess (9) in which said fixing element (10) is freely moveable between said fixing position and said free position and wherein said guide (3) for the pulling member opens in said recess, such that the pulling member (4) extends through this recess.

6. The implant according to claim 1, wherein said control element (14) comprises a control wire which is connected to said fixing element (10).

7. The implant according to claim 6, further comprising a guide (17) for said control wire (14) through which the control wire (14) should extend, wherein said guide opens into said fixing element.

8. The implant according to claim 7, wherein said guide (17) for the control wire (14) forms a tubular channel.

9. The implant according to claim 1, wherein at least said fixing element (10) is made of a memory metal or a bimetal, wherein said control element is formed of a cold or heat source which makes it possible to bring the fixing element (10) at a temperature which is different from a body temperature, such that said fixing element is transformed and is moved from said fixing position into said free position.

10. The implant according to claim 1, wherein said guide (3) for the pulling member (4) forms a tubular channel.

11. The implant according to claim 1, wherein said pulling member (4) is formed of a wire (5).

12. The implant according to claim 1, wherein said pulling member (4) is connected to two or several tissue holders (6).

13. The implant according to claim 1, wherein said guide (3) for the pulling member (4) has an interruption (9) opposite to said fixing element (10), such that, at least in said fixing position, the fixing element (10) extends at least partly in said interruption (9).

14. The implant according to claim 1, wherein said pulling member (4) forms a wire (5) having a series of constrictions and bulges in a longitudinal direction of said wire (5).

15. The implant according to claim 1, wherein said tissue holder (6) is plate-shaped, wire-shaped or elongated and provided with barbs (7) which are to engage in the soft tissue.

16. The implant according to claim 1, wherein in said fixing position, said fixing element (10) and said clamping element (13), at a contact surface between the fixing element (10) and the pulling member (4), and the pulling member (4) and the clamping element (13) respectively, have a bent surface such that, in said fixing position, the fixing element (10), the pulling wire (4) and the clamping element (13) connect in a fitting manner.

17. The implant according to claim 16, wherein in said fixing position, said fixing element (10) and said clamping element (13), at a contact surface between the fixing element (10) and the pulling member (4), and the pulling member (4) and the clamping element (13) respectively, have a smooth surface without any sharp edges.

18. The implant according to claim 1, wherein in said fixing position, said fixing element (10) and said clamping element (13), at a contact surface between the fixing element (10) and the pulling member (4), and the pulling member (4) and the clamping element (13) respectively, have a smooth surface without any sharp edges.

19. The implant according to claim 1, further comprising a projection (23) which cooperates with said fixing element (10), wherein said projection (23) prevents the movement of the fixing element (10) from said fixing position into said free position.

20. An implant for adjusting the position of at least one tissue holder (6) for soft tissue, wherein the implant can be fixed to bone tissue at a distance from said tissue holder (6) and has a guide (3) for an elongate pulling member (4), wherein the pulling member (4) is connected to said tissue holder (6), and wherein the implant comprises a fixing element (10) which can be moved between a fixing position in which the pulling member (4) is clamped by the fixing element (10) and a free position in which said pulling member (4) can freely move through said guide (3), wherein said fixing element (10) cooperates with a control element (14) which makes it possible to move said fixing element (10) between said fixing position and said free position when the implant is attached to said bone tissue and when the implant is covered with soft tissue,     wherein at least said fixing element (10) is made of a memory metal or a bimetal, wherein said control element is formed of a cold or heat source which makes it possible to bring the fixing element (10) at a temperature which is different from a body temperature, such that said fixing element is transformed and is moved from said fixing position into said free position.

21. The implant according to claim 20, comprising a clamping element (13) extending opposite said fixing element (10), wherein said pulling member (4) extends between said clamping element (13) and the fixing element (10), such that in said fixing position, the pulling member (4) is clamped between the fixing element (10) and the clamping element (13), and in said free position, the pulling member (4) can be moved according to its longitudinal direction between the fixing element (10) and the clamping element (13).

22. The implant according to claim 20, wherein said fixing element (10) is formed of a tube (26).

23. The implant according to claim 22, wherein, in said free position, said tube (26) has a substantially circular section such that said pulling member (4) can move substantially freely through this tube (26) according to its longitudinal direction, whereby, in said fixing position, the tube (26) is slightly flattened and compressed such that the pulling member (4) is clamped between opposite parts of the inner wall of the tube (26).

* * * * *